(12) United States Patent
Lundstedt et al.

(10) Patent No.: US 8,372,878 B2
(45) Date of Patent: Feb. 12, 2013

(54) AMINOGUANIDINES AS MELANOCORTIN RECEPTOR LIGANDS

(75) Inventors: Torbjorn Lundstedt, Uppsala (SE); Elisabeth Seifert, Uppsala (SE); Per Lek, Uppsala (SE); Arne Boman, Uppsala (SE)

(73) Assignee: Anamar AB (SE)

( * ) Notice: Subject to any disclaimer, the term of this patent is extended or adjusted under 35 U.S.C. 154(b) by 391 days.

(21) Appl. No.: 12/518,335

(22) PCT Filed: Dec. 13, 2007

(86) PCT No.: PCT/GB2007/004793
§ 371 (c)(1),
(2), (4) Date: Nov. 17, 2009

(87) PCT Pub. No.: WO2008/071980
PCT Pub. Date: Jun. 19, 2008

(65) Prior Publication Data
US 2010/0056641 A1  Mar. 4, 2010

(30) Foreign Application Priority Data
Dec. 14, 2006  (GB) .................................. 0624987.4

(51) Int. Cl.
A61K 31/38 (2006.01)
C07D 339/00 (2006.01)
(52) U.S. Cl. .......................................... 514/431; 549/11
(58) Field of Classification Search .................. 514/431; 549/11
See application file for complete search history.

(56) References Cited

U.S. PATENT DOCUMENTS

| 3,592,935 | A  | 7/1971  | Houlihan et al. |
| 3,896,332 | A  | 7/1975  | Heathcote |
| 3,941,825 | A  | 3/1976  | Tomcufcik |
| 3,982,020 | A  | 9/1976  | Houlihan et al. |
| 4,109,008 | A  | 8/1978  | Cognacq et al. |
| 6,544,541 | B1 | 4/2003  | Zahradka |
| 2004/0106682 | A1 | 6/2004 | Lundstedt et al. |

FOREIGN PATENT DOCUMENTS

| GB | 923398 | | 4/1963 |
| GB | 1223491 | | 2/1971 |
| WO | 9630329 | A1 | 10/1996 |
| WO | 9921571 | | 5/1999 |
| WO | 9955679 | | 11/1999 |
| WO | 9964002 | | 12/1999 |
| WO | 0105401 | A1 | 1/2001 |
| WO | 0125192 | A1 | 4/2001 |
| WO | 0155106 | A2 | 8/2001 |
| WO | 0155107 | A2 | 8/2001 |
| WO | 0155109 | A1 | 8/2001 |
| WO | 0166106 | A2 | 8/2001 |
| WO | 0212166 | A2 | 2/2002 |
| WO | 0212178 | A1 | 2/2002 |
| WO | WO02/11715 | A2 | 2/2002 |
| WO | 0218327 | A2 | 3/2002 |
| WO | 02081430 | A2 | 10/2002 |
| WO | 03009847 | A1 | 2/2003 |
| WO | 03031410 | A1 | 4/2003 |
| WO | 03061660 | A1 | 7/2003 |

OTHER PUBLICATIONS

King, Med. Chem., (1994) pp. 206-208.*
AT 190941B, dated Jul. 25, 1957, Applicant Chemie Linz Ag, English Abstract.
Cavallini, et al.; "Antibacterial Agents. Some New Guanylhydrazone Derivatives"; Journal of Medicinal and Pharmaceutical Chemistry; 4(1); pp. 177-182; (1961).
International Search Report and Written Opinion; International Application No. PCT/GB2007/004793; International Filing Date Dec. 13, 2007; Agent's File Reference No. 86.91212/01; Date of Mailing Feb. 15, 2008; 13 pages.
Kuehmstedt et al.; Pharmazie 29(4); pp. 252-256; with English abstract; (1974).
Mantegazza, et al.; "Antibacterial Activity of Some Guanylhydrazones"; Antibiotics and Chemotherapy; 11(6); pp. 405-408 (1961).

* cited by examiner

Primary Examiner — Taofiq A Solola
(74) Attorney, Agent, or Firm — Cantor Colburn LLP

(57) ABSTRACT

There are described compounds of general formula (I) and isomeric forms thereof wherein n is 0, 1, 2 or 3, saturated or unsaturated; most preferably at least one of $R_1$ to $R_5$ represents halogen; at least one of $R_1$, $R_2$, $R_3$, $R_4$ and $R_5$ is selected from —S—R or —COOR, or two or more Of $R_1$-$R_5$ comprise a linking group such as —S—$(CH2)_m$S—, where m is 1, 2 or 3 and R is selected from alkyl having 1 to 5 carbon atoms, cycloalkyl having 3-6 carbon atoms, hydroxy, and aryl having 6 to 10 carbon atoms, such groups being optionally substituted, and when $R_1$ is selected from —S—R, then at least one of $R_2$, $R_3$ and $R_5$ is most preferably selected from halogen; and $R_1$, $R_2$, $R_3$, $R_4$ and $R_5$ are otherwise the same or different and are selected from hydrogen, halogen, alkyl having 1 to 5 carbon atoms, electron donor groups such as alkoxy having 1-5 carbon atoms or hydroxy, electron acceptor groups selected from cyano, nitro, trifluoroalkyl or amide; alkylamino, benzoyloxy, nitroxy, phenyl or sulpho; and pharmacologically acceptable salts thereof. Compounds described have activity on the melanocortin receptors and have application in the treatment of a wide range of inflammatory, arthritic or central nerve regeneration conditions.

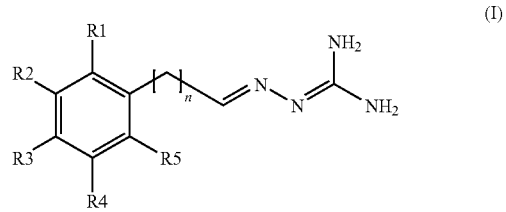

(I)

10 Claims, No Drawings

AMINOGUANIDINES AS MELANOCORTIN RECEPTOR LIGANDS

CROSS-REFERENCE TO RELATED APPLICATIONS

This application is a 371 of PCTGB2007004793 filed Dec. 13, 2007, which claims the benefit of the filing date of Dec. 14, 2006 to Great Britain application No. 0624987.4 under provisions of 35 U.S.C. 119 and the International Convention for the protection of Industrial Property.

The present invention relates to compounds for the treatment of inflammation and autoimmune disorders associated with the melanocortin receptors or related systems, e.g. the melanocyte stimulating hormones.

A number of large linear and cyclic peptides are known in the art which show high specific binding to melanocortin (MC) receptors. The agonistic and/or antagonistic properties of these peptides are also known. See for example "Melanocortin Receptor ligands and methods of using same" by Dooley, Girten and Houghten (WO99/21571). A number of patent applications have been published which describe small molecules showing activity on the MC receptors, see for example WO9955679, WO9964002, WO0105401, WO0125192, WO01055107, WO01055109, WO01055106, WO0212178, WO0212166, WO0218327 and WO03009847, WO03061660 WO03031410. Other examples of pharmacologically active guanidines known in the art are described in U.S. Pat. No. 3,982,020 and GB1223491. Other application areas are also known in the art and are described in U.S. Pat. No. 3,896,332, DE1165013, and U.S. Pat. No. 3,941,825. Low molecular weight compounds have also been reviewed in the literature, see Sebhat et al., *Ann. Rep. Med. Chem.* 38, 31-40, 2003, Speake, et al., *Expert Opin. Ther. Patents* 12, 1631-1638, 2002, Andersson, et al. *Expert Opin. Ther. Patents* 11, 1583-1592, 2001 and references cited therein.

We have now found a range of novel benzylideneaminoguanidines and allylideneaminoguanidines which have activity at the MC-receptors and which can be used to treat inflammation and autoimmune disorders.

In one aspect of the present invention we provide compounds of the general formula (I). Such compounds may act as ligands to the melanocortin receptors and/or for treatment of disorders in the melanocortin system:

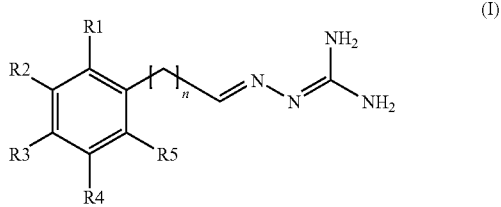

(I)

and isomeric forms thereof
wherein n is 0, 1, 2 or 3, and preferably 0 or 1 saturated or unsaturated;
at least one of $R_1$-$R_5$ is selected from halogen:
at least one of $R_1$, $R_2$, $R_3$, $R_4$ and $R_5$ is selected from —S—R or —COOR, or two or more of $R_1$-$R_5$ comprise a linking group such as —S—$(CH_2)_m$—S—, where m is 1, 2 or 3 and R is selected from alkyl having 1 to 5 carbon atoms, alkoxy having 1-5 carbon atoms; cycloalkyl having 3-6 carbon atoms and aryl having 6 to 10 carbon atoms, and wherein when $R_1$ is selected from —S—R, then at least one of $R_2$, $R_3$ and $R_5$ is selected from halogen;
and $R_1$, $R_2$, $R_3$, $R_4$ and $R_5$ are otherwise the same or different and are selected from hydrogen, halogen, alkyl having 1 to 5 carbon atoms, electron donor groups such as alkoxy having 1-5 carbon atoms or hydroxy, electron acceptor groups selected from cyano, nitro, trifluoroalkyl or amide; alkylamino, benzoyloxy, nitroxy, phenyl or sulpho;
and pharmacologically acceptable salts thereof.

The linking group when present is a preferably a methylenedithio group, particularly preferably a 2,3-, 3,4- or 4,5-methylenedithio group.

When used in the foregoing definitions, the term alkyl is meant to include straight or branched chain hydrocarbon groups. Preferably, the "alkyl having 1 to 5 carbon atoms" is a lower alkyl such as methyl, ethyl, propyl or iso-propyl.

The term alkoxy is meant to include straight or branched chain alkoxy groups. Preferably, the "alkoxy having 1 to 5 carbon atoms" is a lower alkoxy such as methoxy, ethoxy, propoxy or iso-propoxy. Alternatively, two of $R_1$ to $R_5$ may also comprise an oxygen-containing linking group to form a heterocyclic ring, such as with —O—$(CH_2)_m$—O—, where m is as defined above.

The term halogen includes fluoro, chloro, bromo and iodo. Preferably, the halogen is fluoro or chloro.

Preferably, the trifluoroalkyl is trifluoromethyl, trifluoroethyl, trifluoropropyl or trifluoroiso-propyl.

The term "alkylamino" refers preferably to groups having 2-6 carbon atoms, particularly dialkylamino groups, and most preferably dimethylamino or diethylamino.

The compounds of formula (I) have basic properties and, consequently, they may be converted to their therapeutically active pharmaceutically acceptable acid addition salts by treatment with appropriate acids, e.g. inorganic acids such as hydrochloric, hydrobromic, hydroiodic, sulphuric, nitric and phosphoric acid, or organic acids such as acetic, propanoic, glycolic, lactic, malonic, succinic, fumaric, tartaric, citric, palmoic or para-toluene-sulphonic acid.

Conversely, the salt form may be converted into the free base form by treatment with alkali.

The present invention relates also to the use of benzylideneaminoguanidines and allylideneaminoguanidines in therapy. Compounds of formula (I) above, but in which n is 0, 1, 2 or 3, and preferably 0 or 1, saturated or unsaturated;
at least one of $R_1$, $R_2$, $R_3$, $R_4$ and $R_5$ is selected from —S—R and —COOR, or two or more of $R_1$-$R_5$ comprise a linking group such as —S—$(CH_2)_m$—S— where m is 1, 2 or 3;
R is selected from alkyl having 1 to 5 carbon atoms, alkoxy having 1-5 carbon atoms; cycloalkyl having 3-6 carbon atoms and aryl having 6 to 10 carbon atoms, such groups being optionally substituted.
and $R_1$, $R_2$, $R_3$, $R_4$ and $R_5$ are otherwise the same or different and are selected from hydrogen, halogen, alkyl having 1 to 5 carbon atoms, electron donor groups such as alkoxy having 1-5 carbon atoms or hydroxy, electron acceptor groups selected from cyano, nitro, trifluoroalkyl or amide; alkylamino, benzoyloxy, nitroxy, phenyl or sulpho;
and pharmacologically acceptable salts thereof,
which compounds are herein designated compounds (IA), have been biologically tested in the melanocortin system and have surprisingly been shown to be capable of binding to melanocortin receptors as well as showing activity in functional assays. Suprisingly such compounds have shown a lower acute toxicity even though they have a higher uptake compared to compounds known in the prior art.

Preferred compounds of formula (IA) for use in therapy are those of formula (I) as defined above, including the preferences expressed herein.

Some of the compounds of formula (IA) of the present invention are either agonists or antagonists of a specific MC-receptor or of a number of MC-receptors, e.g. MC1, MC3, MC4 or/and MC5 receptors.

MC-receptors are linked to a variety of physiological actions that are thought to be mediated by distinct subtypes of the MC-receptors. In many cases, however, it is not entirely clear which of the subtypes is responsible for the effect.

It has long been known that MSH-peptides may affect many different processes such as motivation, learning, memory, behaviour (including feeding and sexual), inflammation (including immunostimulatory and immunosuppressive), body temperature, pain perception, blood pressure, heart rate, vascular tone, brain blood flow, trophic effects in different organs, nerve growth, placental development, endocrine and exocrine functions, aldosterone synthesis and release, thyroxin release, spermatogenesis, ovarian weight, prolactin and FSH secretion, effects on other hormones, uterine bleeding in women, sebum and pheromone secretion, blood glucose levels, intrauterine foetal growth, as well as other events surrounding parturition and natriuresis (Eberle, AN: The melanotropins: Chemistry, physiology and mechanisms of action. Basel: Karger, Switzerland. 1988, ISBN 3-8055-4678-5; Gruber, and Callahan, Am. J. Physiol. 1989, 257, R681-R694; De Wildt et al., J. Cardiovascular Pharmacology. 1995, 25, 898-905), as well as inducing natriuresis (Lin et al., Hypertension. 1987, 10, 619-627).

It is also well-known that the immunomodulatory action of α-MSH includes both immunostimulatory and immunosuppressive effects. Several studies have shown that α-MSH antagonizes the effects of pro-inflammatory cytokines such as IL-1α, IL-1β, IL-6 and TNFα, and induces the production of the anti-inflammatory cytokine, IL-10 (for review see Catania & Lipton, 1993).

Compounds of formula (I), (IA) and/or their pharmaceutically acceptable salts have valuable pharmacological properties, making them useful for the treatment of inflammation such as inflammations related to the production of nitric oxide, inflammation related to increased amounts (upregulated amounts) of inducible nitric oxide synthase, inflammation related to activation of transcriptional activators, inflammation related to nuclear factor kappa beta, inflammation related to macrophages, neutrophils, monocytes, keratinocytes, fibroblasts, melanocytes, pigment cells and endothelial cells, and inflammation related to increased production and/or release of inflammatory cytokines, such as e.g. interleukins, in particular interleukin 1 (IL-1), interleukin 6 (IL-6) and tumor necrosis factor α (TNF-α).

In the present specification, "increased production" refers to increased formation, increased release, or increased amount of an endogenous compound locally, regionally or systemically in a patient compared to the amount of said endogenous compound in a healthy individual. In the present specification, "upregulated" refers to an increased activity or amount of the compound compared with that in a healthy individual.

In very specific embodiments of the invention, a compound of formula (I) or (IA) of the invention may be administered for the prevention or therapeutic treatment of inflammatory diseases of the skin (including the dermis and epidermis) of any origin, including skin diseases having an inflammatory component. Specific examples of this embodiment of the invention include treatment of contact dermatitis of the skin, sunburns of the skin, burns of any cause, and inflammation of the skin caused by chemical agents, psoriasis, vasculitis, pyoderma gangrenosum, discoid lupus erythematosus, eczema, pustulosis palmo-plantaris, and phemphigus vulgaris.

Also comprised by the invention is the administration of a compound of formula (I), (IA) or a pharmacologically acceptable salt thereof for the treatment of an inflammatory disease in the abdomen, including an abdominal disease having an inflammatory component. Specific examples of the treatment of such a disease with a compound of the invention are gastritis, including one of unknown origin, gastritis perniciosa (atrophic gastritis), ulcerous colitis (colitis ulcerosa), morbus Crohn, systemic sclerosis, ulcus duodeni, coeliac disease, oesophagitis and ulcus ventriculi.

Comprised by the invention is also the administration of a compound of formula (I), (IA) or a pharmacologically acceptable salt thereof for the treatment of systemic or general and/or local immunological diseases, including those of an autoimmune nature, and other inflammatory and/or arthritic conditions or diseases of a general nature. Specific examples include treatment of rheumatoid arthritis, psoriatic arthritis, systemic sclerosis, polymyalgia rheumatica, Wegener's granulomatosis, sarcoidosis, eosinophilic fasceitis, reactive arthritis, Bechterew's disease, systemic lupus erythematosus, arteritis temporalis, Behcet's disease, morbus Burger, Good Pastures' syndrome, eosinophilic granuloma, fibromyalgia, myositis, and mixed connective tissue disease. Included therein is also arthritis, including arthritis of unknown origin.

Further included in the invention is administration of a compound of formula (I), (IA) or a pharmacologically acceptable salt thereof for the treatment of a disease of the peripheral and/or central nervous system related to inflammation. Included in this aspect of the invention is the treatment of cerebral vasculitis, multiple sclerosis, autoimmune ophthalmitis and polyneuropathia. Comprised by the invention is also the administration of such a compound for the treatment of an inflammation of the central nervous system to prevent apoptotic cell death. Moreover, as some compounds show a distinct ability to induce nerve regeneration, positive treatment effects are often seen in central nervous system diseases involving damage of cells in this region. This aspect of the invention also includes treatment of traumatic injuries to the central nervous system, brain edema, multiple sclerosis, Alzheimer's disease, bacterial and viral infections in the central nervous system, stroke, and haemorrhagia in the central nervous system.

Comprised by the invention is also the administration of a compound of formula (I), (IA) or a pharmacologically acceptable salt thereof for the treatment of diseases of the eye and tear glands related to inflammation. Specific examples of such diseases comprise anterior and posterior uveitis, retinal vasculitis, optic neuritis, optic neuromyelitis, Wegener's granulomatosis, Sjögren's syndrome, episcleritis, scleritis, sarcoidosis affecting the eye and polychondritis affecting the eye.

The invention also relates to methods for the manufacture of compounds of formula (I), (IA) and to pharmaceutical preparations comprising one or more of the compounds of formula (I) or (IA) in admixture with a pharmaceutically acceptable carrier, diluent or excipient. It relates also to their uses for various medical and veterinary practices related to melanocyte stimulating hormone receptors.

Some of the compounds of the invention have an effect on xanthine oxidase in mammals, including humans.

METHODS OF PREPARATION

Examples

The following examples are intended to illustrate but not to limit the scope of the invention, although the compounds named are of particular interest for the intended purposes. These compounds have been designated by a number code, a:b, where a means the number of example, wherein the preparation of the compound is described, and b refers to the order of the compound prepared according to that example. Thus example 1:2 means the second compound prepared analogously according to Method 1 (see example 1).

Example 1

The compounds having the general formula (I) or (IA) wherein n is 0, 1, 2 or 3 saturated or unsaturated may be prepared by the following general method.
Method 1.

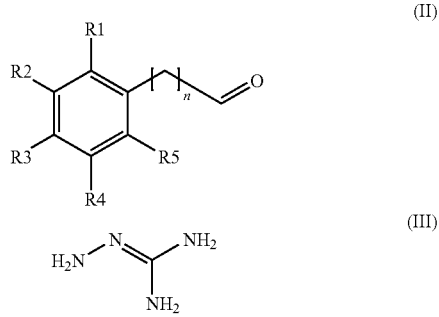

A compound of formula (II) wherein $R_1$, $R_2$, $R_3$, $R_4$ and $R_5$ are as previously defined for formula (IA), is reacted with aminoguanidine (III) and a compound of formula (I) or (IA) is obtained. The reaction may be carried out in an organic solvent, e.g a lower alkanol such as methanol and at elevated temperature, desirably under reflux.

IR, NMR, MS and elementary analysis have confirmed the structures of the compounds. When melting points (m.p.) are given, these are uncorrected.
Preparation of Compound 1:1
A solution of 2-methylthio-3-chlorobenzaldehyde (1.0 g, 5 mmol), aminoguanidine bicarbonate (0.68 g, 5 mmol) and acetic acid (1 ml), in 15 ml of methanol was heated at reflux for 10 min. The reaction mixture was cooled down to 0° C. and the residue was filtered off. The filtrate was evaporated under vacuum and the product was crystallised from ethanol. Yield of the title compound 1:1 was 1.1 g (70%).
Preparation of Compounds 1:2
Compounds 1:2-1:12 were prepared using essentially the same approach as for 1:1 by using a procedure analogous to Method 1. Compounds with their data was as follows:
1:1  N-(2-Methylthio-3-chlorobenzylideneamino)guanidine hydrochloride m.p. 179-181° C.
1:2  N-(2-Chloro-4-Methoxy-3-methylthiobenzylideneamino)guanidine
1:3  N-(2-Chloro-(3-ethoxycarbonyl)-benzylideneamino) guanidine trifluoroacetate m.p. 146°
1:4  N-(2-Chloro-3-Methoxy-4-methylthiobenzylideneamino)guanidine
1:5  N-(2-Chloro-3,4-dimethylthiobenzylideneamino)guanidine
1:6  N-(5-Chloro-2,3-dihydro-benzo[1,4]dithiin-6-ylmethyleneamino)-guanidine
1:7  N-(2-Methylthio-3-chlorophenylpropylideneamino) guanidine
1:8  N-(2-Chloro-4-Methoxy-3-methylthiophenylpropylideneamino)guanidine
1:9  N-(2-Chloro-(3-ethoxycarbonyl)-phenylpropylideneamino)guanidine
1:10  N-(2-Chloro-3-Methoxy-4-methylthiophenylpropylideneamino)guanidine
1:11  N-(2-Chloro-3,4-dimethylthiophenylpropylideneamino)guanidine
1:12  N-[3-(5-Chloro-2,3-dihydro-benzo[1,4]dithiin-6-yl)-allylideneamino]-guanidine Example 2

This example illustrates the potency of compounds of formula (I) and their therapeutically active acid addition salts for treatment of mental disorders.
Test 1. Affinity for the MC1-Receptor
The binding assay was carried out essentially as described by Lunec et al, Melanoma Res 1992; 2; 5-12, using $I^{125}$-NDP-$\alpha$MSH as ligand.
Test 2. Affinity for the MC3-Receptors, the MC4-Receptors and the MC5-Receptors
The binding assays were carried out essentially as described by Szardenings et al, J Biol Chem 1997; 272; 27943-27948 and Schiöth et al, FEBS Lett 1997; 410; 223-228 using $I^{125}$-NDP-$\alpha$MSH as ligand.
Test 3. cAMP
The stimulation of cAMP was carried out essentially as described by Schiöth et al, Br J Pharmacol 1998; 124; 75-82.

TABLE 1

| | Affinity for MC-receptors | | | |
| --- | --- | --- | --- | --- |
| | Ki(μM) | | | |
| Compound | MC1 | MC3 | MC4 | MC5 |
| 1:1 | 0.7 | 19.7 | 0.6 | 19.7 |
| 1:3 | 3.4 | | | |

TABLE 1b

| | Influence on cAMP | | | |
| --- | --- | --- | --- | --- |
| | MC1c | MC3c | MC4c | MC5c |
| 1:1 | 1 | 2 | 13 | 1 |
| 1:3 | 0 | 0 | 7 | 0 |

Example 3

Synovial Fibroblasts

Study design: From rats with antigen induced arthritis, the hyperproliferative synovium, pannus, was taken from the inflamed knee day four after disease onset. The pannus tissue was cut to small pieces in PBS with PEST (100 IU penicillin, 100 μg/ml streptomycin) and Fungizone (2.5μ/ml) (all from InVitrogen, Sweden), before incubation in collagenase (400 U/ml, Worthington, USA) for 3 hours at 37° C., 5% CO2. Cells were centrifuged (8 min., rt, 1100 rpm.) and suspended in RPMI 1640 supplemented with 10% FCS (InVitrogen, Sweden), PEST and Fungizone and seeded in a 25 cm2 flask at 37° C., 5% CO2. The following day, cells were rinsed once with medium and further incubated. When confluent, cells were trypsinated for 1 min (0.25% Trypsin with EDTA, InVitrogen, Sweden) counted and seeded in 96 well plates, 10000 cells/well/200 μl.

After 24 hours, the medium was changed, and the cells were stimulated with human recombinant IL-1a, 50 ng/ml (Roche, Sweden). The peptide AM0001 (Schaefer, Denmark) was tested in triplets in the concentration interval 50-400 µM. After 72 hour incubation at 37° C., 5% CO2, the medium was collected for measurement of NO (Griess reaction) and IL-6 was analyzed by an ELISA, according to the manufacturer's instructions (BD Biosciences, USA).

Example 4

Cartilage Explants

The effect of the compounds on NO release in IL-1 stimulated cartilage was measured as described below.

A skinned bovine nose (from cows 18-24 months old) was collected at Hörby slaughter house (Team Ugglarp, Sweden). The septum inside the nose was cut out and the mucosa and the perichondrium was removed before the cartilage was placed in PBS with PEST (100 IU penicillin, 100 mg/ml streptomycin) and 2.5 µg/ml Fungizone (all from Invitrogen, Sweden) for 2 hours at rt. Two mm pieces were punched out of the cartilage. Each piece was placed in a 24-well cell culture plate (Falcon, Sweden) containing 1 ml cell culture medium, HAMs F12 (Invitrogen, Sweden) supplemented with 10 µg/ml BSA, 25 mg/ml ascorbate (both from Sigma, Sweden), PEST (100 IU penicillin, 100 mg/ml streptomycin) and 2.5 ug/ml Fungizone. After 24 hours, the medium was changed and the cartilage pieces were stimulated with human recombinant IL-1a, 10 ng/ml (Roche, Sweden). The test compounds was tested in triplets at a suitable concentration The cartilage tissue was incubated for another six days, mediums were exchanged every third day. On each occasion the mediums were collected for measurement of NO (Griess reaction).

Example 5

Anti Inflammatory Effects

Control

Female BALB/c mice (weight 20-22 g) were sensitized by treatment of the shaved abdomen with 30 µl of 0.5% 2,4-dinitrofluorobenzene (DNFB). After 4 days they were challenged with 10 µl of 0.3% DNFB to the paw. The unchallenged mice paws served as a control. Twenty-four hours after the last challenge, the differences in paws weight were determined as an indicator of the inflammation (paw edema).

Prednisolone Control

Mice were treated as the control but were additionally injected intraperitoneally (i.p.) prednisolone (20 mg/kg) two hours before sensitization (day 0) and the same dose was administered repeatedly after sensitization ring four consecutive days. The paw edema inhibition was measured as described above.

Study of New Compounds

Mice were treated as the control but were additionally injected i.p. with various doses (0.05, 0.15 or 0.25, 0.375, 0.5, 0.75 and in later studies also 1.5, 3 and occasionally 6 mg/kg) of each compounds two hours before sensitization (day 0) and the same dose was administered repeatedly after sensitization during four consecutive days. The paw edema inhibition as described above. Groups containing at least 10 mice each were used for all experiments.

Blood analysis was carried out using the QBC.® Autoread™ Plus & QBC.® Accutube System (Becton Dickinson). In all cases blood samples were collected twenty-four hours after the last challenge.

Example 6

Antigen Induced Arthritis (AIA)

Antigen Induced Arthritis (AIA) in the rat is a well reproducible monoarthritis model.

An intraarticular injection of the antigen methylated bovine serum albumin (mBSA) in the knee joint in sensitised animals induces an inflammatory response. The formation of pannus tissue, which invades the synovium, spreads over the articular cartilage and grows into the bone, leading to tissue erosion and remodeling AIA responds well to compounds used for standard clinical treatment of human arthritis. Therefore this model is appropriate for the evaluation of the effects of new compounds on joint inflammation and cartilage/bone degradation. The test compounds can be administered locally or systemically. The features of the arthritis can be followed and evaluated by measuring knee joint swelling, by functional scoring and histological analysis. Since it is a monoarthritis model, the level of inflammatory serum markers may be difficult to detect. The AIA model also serves as a source for the production of synoviocytes for in vitro culturing, in order to gain further insight in the synovial matrix composition and for drug screening purposes.

Example 7

Collagen-Induced Arthritis (CIA)

Collagen-induced arthritis (CIA) in the mouse is the most common experimental model for rheumatoid arthritis, with several features in common with the human disease. Autologous or heterologous collagen type II (CII) emulsified in Freund's Complete Adjuvant induces a polyarthritis, with edema of the synovial tissue, synovial cell proliferation, inflammatory cell infiltration and erosions of cartilage and bone. The test compounds should be administered systemically. The features of polyarthritis can be evaluated by scoring the signs of arthritis, histological analysis and by measurements of serum biomarkers. The bone mineral content and density may also be analysed by mouse densitometry (PIXIMUS).

Suitable forms of pharmaceutical preparation for administration include for example tablets, capsules, solutions, syrups, or emulsions. The content of the pharmaceutically effective compound(s) in each case should desirably be in the range from 0.1 to 5 wt. %, of the total composition.

The preparations may be administered orally in the form of a tablet, as a powder, as a powder in a capsule (e.g. a hard gelatine capsule), as a solution or suspension.

It is preferable if the compounds of formula (I) or (IA) are administered orally. Suitable tablets may be obtained, for example, by mixing the active substance(s) with known carriers, diluents or excipients, such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may suitably be prepared by coating cores produced similarly to the tablets with substances normally used for tablet coatings, for example collidone or shellac, gum arabic, talc, titanium dioxide or sugar. The tablet coating may consist of a number of layers to achieve delayed release, possibly using the excipients mentioned above for the tablets.

Syrups containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may contain, in addition to the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions, the active substances may be combined with various flavour enhancers or colourings in addition to the excipients mentioned above.

Example 8

The following formulations are representative for all of the pharmacologically active compounds of the invention.

Example of a Preparation Comprising a Capsule

|  | Per capsule |
| --- | --- |
| Active ingredient, as salt | 5 mg |
| Lactose | 250 mg |
| Starch | 120 mg |
| Magnesium stearate | 5 mg |
| Total up to | 380 mg |

In case higher amounts of active ingredient, the amount of lactose used may be reduced.

Example of a Suitable Tablet Formulation.

|  | Per tablet |
| --- | --- |
| Active ingredient, as salt | 5 mg |
| Potato starch | 238 mg |
| Colloidal Silica | 10 mg |
| Talc | 20 mg |
| Magnesium stearate | 2 mg |
| 5% aqueous solution of gelatine | 25 mg |
| Total up to | 300 mg |

A solution for parenteral administration by injection can be prepared in an aqueous solution of a water-soluble pharmaceutically acceptable acid addition salt of the active substance preferably in a concentration of 0.1% to about 5% by weight. These solutions may also contain stabilising agents and/or buffering agents.

The invention claimed is:
1. A compound of general formula (I)

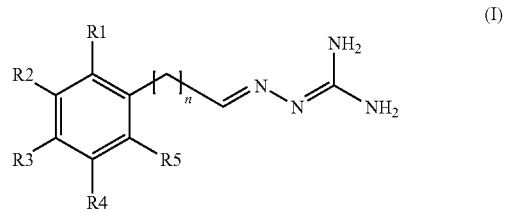

(I)

and isomeric forms thereof
wherein n is 0, 1, 2 or 3, with saturated or unsaturated bonds;
at least one of $R_1$ to $R_5$ represents halogen;
at least one of $R_1$, $R_2$, $R_3$, $R_4$ and $R_5$ is —S—R, or two of $R_1$-$R_5$ form a linking group —S—$(CH_2)_m$—S—, where m is 1, 2 or 3; and
R is selected from alkyl having 1 to 5 carbon atoms, cycloalkyl having 3-6 carbon atoms, hydroxy, and aryl having 6 to 10 carbon atoms, such groups being optionally substituted;
and wherein when $R_1$ is —S—R, then at least one of $R_2$, $R_3$ or $R_5$ is selected from halogen;
and $R_1$, $R_2$, $R_3$, $R_4$ and $R_5$ are otherwise the same or different and are selected from hydrogen, halogen, alkyl having 1 to 5 carbon atoms, alkoxy having 1-5 carbon atoms or hydroxy, cyano, nitro, trifluoroalkyl or amide; alkylamino, benzoyloxy, nitroxy, phenyl and sulpho;
and pharmacologically acceptable salts thereof.
2. A compound as claimed in claim 1 wherein n is 0 or 1.
3. A compound as claimed in claim 1 wherein the linking group is a methylenedithio group.
4. A compound as claimed in claim 3 wherein the linking group is a 2,3-, 3,4- or 4,5-methylenedithio group.
5. A compound as claimed in claim 1 wherein the halogen is fluoro or chloro.
6. A compound having one of the following formulae:
1:1 N-(2-Methylthio-3-chlorobenzylideneamino)guanidine
1:2 N-(2-Chloro-4-Methoxy-3-methylthiobenzylideneamino)guanidine
1:4 N-(2-Chloro-3-Methoxy-4-methylthiobenzylideneamino)guanidine 1:5 N-(2-Chloro-3,4-dimethylthiobenzylideneamino) guanidine 1:6 N-(5-Chloro-2,3-dihydro-benzo[1,4]dithiin-6-ylmethyleneamino)-guanidine 1:7 N-(2-Methylthio-3-chlorophenylpropylideneamino) guanidine 1:8 N-(2-Chloro-4-Methoxy-3-methylthiophenylpropylideneamino)guanidine 1:10 N-(2-Chloro-3-Methoxy-4-methylthiophenylpropyliideneamino)guanidine 1:11 N-(2-Chloro-3,4-dimethylthiophenylpropylideneamino)guanidine 1:12 N-[3-(5-Chloro-2,3-dihydro-benzo[1,4]dithiin-6-yl)-allylideneamino]-guanidine or a pharmacologically acceptable salt thereof.

7. A pharmaceutical composition comprising a compound as claimed in claim 1, together with one or more pharmaceutically acceptable adjuvants, carriers or excipients.

8. A method of treating inflammation, an arthritic condition or for inducing central nerve regeneration which comprises administering to a subject in need thereof an effective amount of a compound (IA)

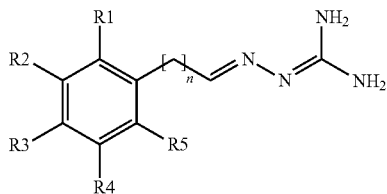

wherein n is 0, 1, 2 or 3, with saturated or unsaturated bonds;

at least one of $R_1$, $R_2$, $R_3$, $R_4$ and $R_5$ is —S—R, or two of $R_1$-$R_5$ form a linking group —S—$(CH_2)_m$—S— where m is 1, 2 or 3;

R is selected from alkyl having 1 to 5 carbon atoms, alkoxy having 1-5 carbon atoms; cycloalkyl having 3-6 carbon atoms; and aryl having 6 to 10 carbon atoms, such groups being optionally substituted and $R_1$, $R_2$, $R_3$, $R_4$ and $R_5$ are otherwise the same or different and are selected from hydrogen, halogen, alkyl having 1 to 5 carbon atoms, alkoxy having 1 to 5 carbon atoms or hydroxy, cyano, nitro, trifluoroalkyl or amide; alkylamino, benzoyloxy, nitroxy, phenyl and sulpho;

and pharmacologically acceptable salts thereof.

9. The method of claim 8, wherein the arthritic condition is arthritis.

10. A method of treating pain which comprises administering to a subject in need thereof an effective amount of a compound (IA)

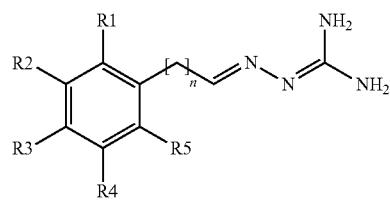

wherein n is 0, 1, 2 or 3, with saturated or unsaturated bonds;

at least one of $R_1$, $R_2$, $R_3$, $R_4$ and $R_5$ is —S—R, or two of $R_1$-$R_5$ form a linking group —S—$(CH_2)_m$—S— where m is 1, 2 or 3;

R is selected from alkyl having 1 to 5 carbon atoms, alkoxy having 1-5 carbon atoms;

cycloalkyl having 3-6 carbon atoms; and aryl having 6 to 10 carbon atoms, such groups being optionally substituted and $R_1$, $R_2$, $R_3$, $R_4$ and $R_5$ are otherwise the same or different and are selected from hydrogen, halogen, alkyl having 1 to 5 carbon atoms, alkoxy having 1 to 5 carbon atoms or hydroxy, cyano, nitro, trifluoroalkyl or amide; alkylamino, benzoyloxy, nitroxy, phenyl and sulpho;

and pharmacologically acceptable salts thereof.

\* \* \* \* \*